United States Patent [19]  [11] 4,002,614
Anner et al.  [45] Jan. 11, 1977

[54] HALOGENATED 19-NORSTEROIDS
[75] Inventors: Georg Anner, Basel; Peter Wieland, Oberwil, both of Switzerland
[73] Assignee: Ciba-Geigy Corporation, Ardsley, N.Y.
[22] Filed: Sept. 25, 1975
[21] Appl. No.: 616,518

Related U.S. Application Data
[63] Continuation of Ser. No. 442,931, Feb. 15, 1974, abandoned.

[30] Foreign Application Priority Data
Feb. 28, 1973 Switzerland .................. 2950/73
Dec. 20, 1973 Switzerland .................. 17898/73

[52] U.S. Cl. ............. 260/239.55 D; 260/239.55 R; 260/397.47; 424/241
[51] Int. Cl.² ......................... C07J 21/00
[58] Field of Search ................. 260/239.55 D

[56] References Cited
UNITED STATES PATENTS
3,763,145  10/1973  Anner et al. ............... 260/239.55

Primary Examiner—Elbert L. Roberts
Attorney, Agent, or Firm—Joseph G. Kolodny; John J. Maitner; Theodore O. Groeger

[57] ABSTRACT

21-Fluoro-19-norpregnadienes of the formula

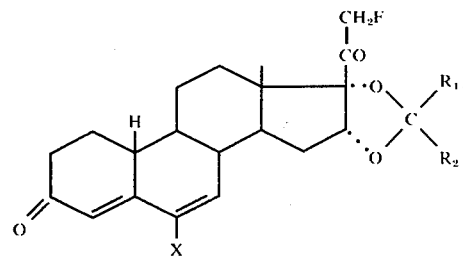

wherein X represents hydrogen, lower alkyl, chlorine or fluorine and $R_1$ and $R_2$ each individually denote a hydrogen atom or an acyclic or carbocyclic hydrocarbon radical or both together with the adjacent carbon atom form a cycloaliphatic ring, are useful gestagenic and ovulation-inhibiting agents suitable for oral administration.

4 Claims, No Drawings

HALOGENATED 19-NORSTEROIDS

This is a continuation, of application Ser. No. 442,931, filed Feb. 15, 1974 now abandoned.

The present invention relates to new halogenated 19-norsteroids of the pregnane series, especially 21-fluoro-19-norpregnadiene compounds of the general formula

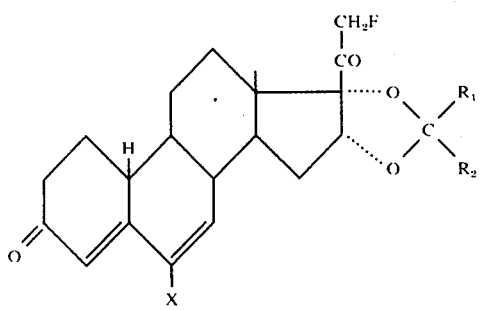

wherein X represents hydrogen, lower alkyl, chlorine or fluorine and $R_1$ and $R_2$ each individually denote a hydrogen atom or an acyclic or carbocyclic hydrocarbon radical or both together with the adjacent carbon atom form a cycloaliphatic ring, and processes for their manufacture.

The substituents $R_1$ and $R_2$ can be identical or different. An acyclic hydrocarbon radical is, in particular, a saturated or unsaturated aliphatic radical with at most 15 carbon atoms, for example an alkyl, alkenyl or alkinyl radical. A carbocyclic hydrocarbon radical is, in particular, a cycloaliphatic or cycloaliphatic-aliphatic radical with, preferably, one cycloaliphatic ring, or an aromatic or araliphatic monocyclic radical. A cycloaliphatic ring is, in particular, a saturated 5-membered or 6-membered ring which can also be substituted by alkyl radicals, for example those mentioned below, above all the cyclopentane and cyclohexane ring.

Alkyl radicals to be mentioned are, in particular, lower alkyl radicals, for example ethyl, n-propyl, i-propyl, n-butyl, i-butyl, sec.-butyl, tert.-butyl and straight and branched pentyl and hexyl radicals, and above all the methyl radical. Lower alkyl radicals which X can represent are in particular those of the radicals mentioned which possess at most 4 carbon atoms and preferably a straight chain, especially an ethyl radical and above all a methyl radical. Possible alkenyl and alkinyl radicals are in particular those which correspond to the abovementioned lower alkyl radicals and carry an unsaturated bond, for example vinyl, allyl, methallyl, ethinyl and propargyl radicals. As cycloaliphatic and cycloaliphatic-aliphatic radicals there should especially be mentioned those derived from a 5-membered or 6-membered saturated ring which can be substituted by the abovementioned lower alkyl radicals, for example lower cycloalkyl radicals, such as cyclopentyl, 2- or 3-methylcyclopentyl, 2,5- or 3,4-dimethylcyclopentyl, cyclohexyl and 2-, 3- or 4-methylcyclohexyl radicals, and lower cycloalkyl-alkyl radicals, such as cycloalkyl-methyl and 2-(cycloalkyl)-ethyl radicals, in which the cyclic part is formed by the abovementioned lower cycloalkyl radicals. The preferred aromatic and araliphatic radicals are, for example, the phenyl, benzyl and 1- and 2-phenylethyl radicals, which can be substituted in positions 2 to 6 by lower alkyl radicals, for example those mentioned above.

The new compounds are, in particular, 16,17-ketals of the corresponding 16α,17α-dihydroxysteroid which are derived from ketones of the formula $R_1$-CO-$R_2$, wherein $R_1$ and $R_2$ represent radicals, containing carbon, and having the abovementioned general and preferred meanings. Particularly preferred ketone components of these ketals are saturated lower aliphatic ketones, for example 2-butanone, 2-pentanone, 3-pentanone, 4-methyl-2-pentanone, 4-heptanone, 5-nonanone and above all acetone, saturated cycloaliphatic ketones, for example cyclopentanone and cyclohexanone, and phenylketones, for example acetophenone or benzophenone. The corresponding 16α,17α-dihydroxysteroid is, in particular, the 21-fluoro-16α,17α-dihydroxy-19-nor-4,6-pregnadiene-3,20-dione, which is optionally substituted in the 6-position by fluorine or above all by chlorine or methyl.

The new compounds of the present invention possess valuable pharmacological properties. Thus, they display a pronounced gestagenic and ovulation-inhibiting action, especially on peroral administration, as can be demonstrated in animal experiments. A progestative action in the Clauberg test on rabbits manifests itself, on peroral administration, at doses as low as 0.01 to 0.1 mg/kg and in the ovulation test on rats at doses of 0.01 to 0.1 mg/kg administered perorally.

Compounds to be singled out particularly are 21-fluoro-16α,17α-dihydroxy-19-nor-4,6-pregnadiene-3,20-dione-16,17-acetonide, 21-fluoro-16α,17α-dihydroxy-6-methyl-19-nor-4,6-pregnadiene-3,20-dione-16,17-acetonide and 6-chloro-21-fluoro-16α,17α-dihydroxy-19-nor-4,6-pregnadiene-3,20-dione-16,17-acetonide which all display a distinct activity in the abovementioned animal experiments even at the lower limit of the indicated dosage range.

By virtue of these properties, the new compounds according to the invention find their use in human and veterinary medicine and as active components in contraceptives for humans and mammals.

The new compounds of the present invention are however also intermediate products for the manufacture of other useful substances, especially pharmacologically active compounds.

The new compounds according to the invention can be manufactured in a manner which is in itself known.

According to one general process, a possible procedure is, for example, to introduce the 6,7-double bond into a compound of the formula

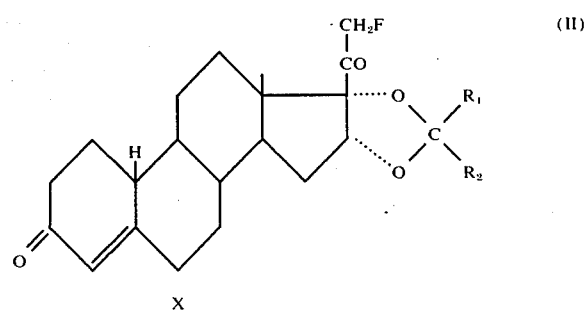

wherein $R_1$, $R_2$ and X have the abovementioned meanings and X can be in the α- or β- configuration.

The introduction of the 6,7-double bond can be realised according to methods which are in themselves known, it being possible to use a one-stage or multistage method. The one-stage, that is to say direct, introduction of the 6,7-double bond is achievable, for example, in accordance with known methods of dehydration by treating the compound of the formula II with a quinone which has a dehydrating action, for example chloranil or especially 2,3-dichloro-5,6-dicyano-1,4-benzoquinone. When using the former, the reaction is preferably carried out at the boil in organic solvents, for example aromatic hydrocarbons, such as benzene or xylene, lower aliphatic alcohols, such as ethanol, propanol or tert.-butyl alcohol, lower aliphatic ketones, such as acetone or 2-butanone, aliphatic esters, such as ethyl acetate, or cyclic ethers, such as dioxane or tetrahydrofurane. When using dichlorodicyanobenzoquinone, the reaction is preferably carried out in the presence of hydrochloric acid at or below room temperature in a water-miscible organic solvent, for example one of those mentioned above.

Instead of the compound of the formula II it is also possible to employ a corresponding 3-enol ether, preferably a lower alkyl enol ether, such as the methyl enol ether or ethyl enol ether. The 3-enol ether is obtainable from a compound of the formula II according to generally known methods, preferably by treatment with a corresponding orthoformic acid ester, using acid catalysis. The 3-enol ether can also be treated with a quinone having a dehydrating action, for example as described above, or can be dehydrated to the desired end product by the action of manganese dioxide, preferably in a halogenated hydrocarbon, such as chloroform or dichloromethane. If the 6,7-double bond is introduced by a multi-stage variant of the process, the elements of a hypohalous acid, such as of hypochlorous or especially hypobromous acid, are allowed to add onto the 3-enol ether and the halogen atom added on is eliminated from the 6α-X,6β-halogen compound, formed as an intermediate, in the form of the corresponding hydrogen halide. The addition reaction is advantageously carried out by treatment with hypochlorous acid or hypobromous acid formed in situ, produced in the reaction mixture from one of its organic derivatives, especially a corresponding N-halogenoamide or halogenoimide, for example bromoacetamide or bromosuccinimide. The reaction is advantageously carried out in organic, water-miscible solvents, for example acetone, dioxane or tetrahydrofurane, in the presence of water and of a lower aliphatic carboxylic acid, for example acetic acid, and optionally also in the presence of an alkali metal salt of this acid, for example in the presence of sodium acetate or potassium acetate. The subsequent elimination of the hydrogen halide is effected, for example, by treatment with a carbonate of a metal of group I or II, preferably with lithium carbonate or calcium carbonate, in a suitable solvent, for example dimethylformamide or hexamethylphosphotriamide, optionally in the presence of a lithium halide.

According to a further method which is in itself known, a possible procedure is to decarboxylate or decarbonylate a compound of the formula

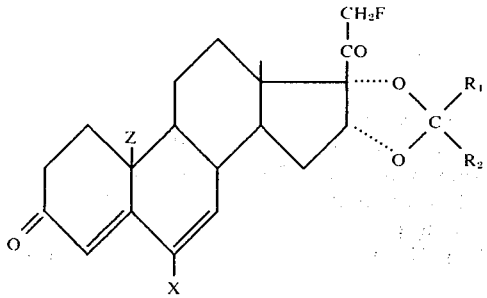

wherein $R_1$, $R_2$ and X have the abovementioned meanings and Z denotes a free carboxyl group or a formyl group.

The elimination of carbon dioxide or carbon monoxide from compounds of the formula III is carried out in a manner which is in itself known. If the group Z is a free carboxyl group, carbon dioxide is eliminated by warming to the decomposition temperature, optionally in a suitable organic solvent. The elimination can also advantageously be facilitated by acid catalysis. If the group Z which is to be split off is the formyl group, carbon monoxide is advantageously eliminated under the catalytic action of bases, especially hydroxides or lower alkoxides of the alkali metals, for example potassium hydroxide or sodium ethylate.

The compounds according to the invention can also be obtained when, in a compound of the formula

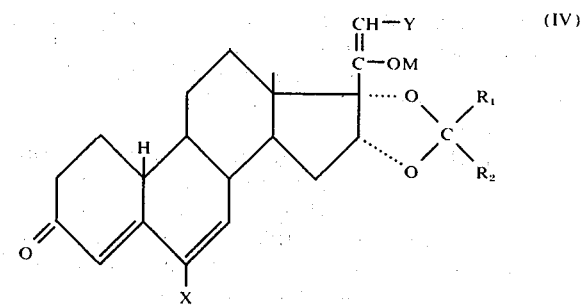

wherein $R_1$, $R_2$ and X have the abovementioned meanings and Y represents a hydrogen atom, a formyl radical or an esterified oxalyl radical, and M represents an alkali metal atom, especially a lithium atom or, if Y denotes the formyl or esterified oxalyl radical, also represents hydrogen, the radical Y is replaced by a fluorine atom, if necessary with temporary protection of the 3-oxo group.

The esterified oxalyl radical is a radical of the formula —CO—COOR$_r$, wherein R$_r$ denotes an aliphatic hydrocarbon radical, preferably a lower alkyl radical, for example one of those mentioned above and especially the methyl or ethyl radical.

The replacement of the radical Y by a fluorine atom takes place in a manner which is in itself known. For example, a possible procedure is to treat the starting substance of the abovementioned formula, or its 3-ketal, with perchloryl fluoride. The treatment with perchloryl fluoride is carried out in a manner which is in itself known, for example by introducing the gaseous reagent into the reaction mixture at room temperature, if necessary whilst cooling. Suitable solvents to be mentioned are especially bases containing nitrogen, for example secondary and tertiary alkylamines, such as diisopropylamine or triethylamine, and heterocyclic bases, such as pyridine, its homologues or quinoline, but also hydrocarbons such as pentane or cyclohexane and above all ethers such as tetrahydrofurane or dioxane.

The starting substances of the abovementioned formula IV are 20(21)-en-20-ol derivatives of the corresponding 20-ketones and are preferably obtainable from the latter by enolisation. If Y denotes the formyl or esterified oxalyl radical, a separate enolisation stage is usually unnecessary due to the favourable equilibrium of the keto and enol form. If Y denotes hydrogen, the enolate of the formula IV can be obtained in a manner which is in itself known, for example from a corresponding 20-ketone by means of an alkali metal amide such as, for example, sodium amide, potassium amide or lithium amide or especially lithium diisopropylamide. At the same time it is advisable temporarily to protect the 3-keto group of the 20-ketones used in a manner which is in itself known, especially by ketalisation, for example with an aliphatic diol, preferably ethylene glycol.

In starting substances in which Y denotes the formyl or esterified oxalyl radical, the replacement of the radical Y by a fluorine atom can also be carried out in two stages in a manner which is in itself known, by reacting the starting substance with an agent which transfers diazo groups, for example a sulphonyl azide, such as p-tosyl azide or p-carboxyphenylsulphonyl azide, and treating the resulting intermediate 21-diazo-20-ketone with hydrogen fluoride in a known manner.

According to another process, a compound of the formula

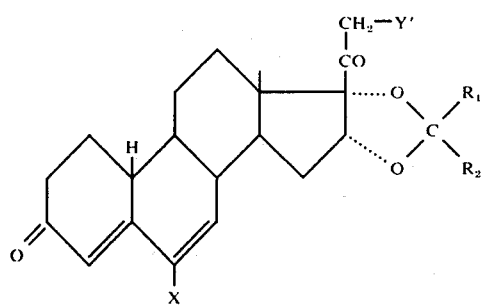

wherein X, $R_1$ and $R_2$ have the abovementioned meanings and Y' denotes a hydroxyl group esterified by hydrobromic acid or by an organic sulphonic acid, is treated with a fluoride of the metals of group I, for example silver fluoride and especially an alkali metal fluoride, preferably potassium fluoride, in a highly polar solvent, for example in acetonitrile or tetramethylenesulphone. This reaction is preferably carried out at the boil of the reaction mixture.

The organic sulphonic acid used to esterify the abovementioned hydroxyl group is, in particular, a monocyclic aromatic sulphonic acid, such as p-toluenesulphonic acid, or preferably a lower aliphatic sulphonic acid, such as, above all, methanesulphonic acid.

The compounds according to the invention can also be prepared, for example, by reacting a corresponding 16,17-diol of the formula

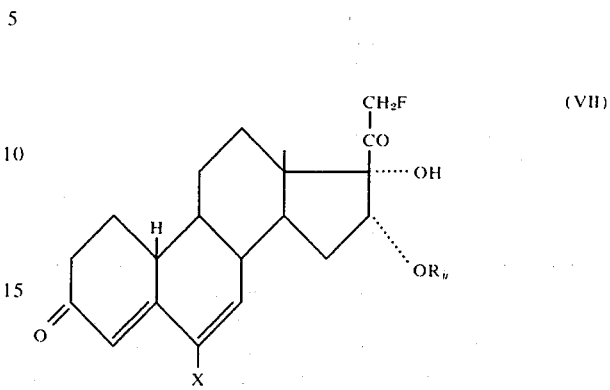

wherein X has the abovementioned meaning and $R_y$ represents a hydrogen atom or a lower alkanoyl radical, for example the acetyl radical, with a carbonyl compound of the formula $R_1$-CO-$R_2$, wherein $R_1$ and $R_2$ have the abovementioned meanings, or with a reactive derivative thereof, in a manner which is in itself known, preferably with acid catalysis.

The reaction can be effected, for example, by treating the corresponding steroid component of the formula VII with the desired carbonyl compound, especially with a ketone, in the presence of a catalytic amount of a strong acid. Possible strong acids are, for example, strong mineral acids, such as hydrochloric acid, sulphuric acids, phosphoric acids and especially perchloric acid, or organic sulphonic acids, such as camphorsulphonic acid, or especially monocyclic aromatic sulphonic acids, such as p-toluenesulphonic acid or sulphosalicyclic acid. In the ketalisation reaction, an excess of the corresponding ketone is usually employed as the solvent, but it is generally also possible to carry out the reaction in a solution in suitable organic solvents, for example halogenated hydrocarbons, such as chloroform, amides, such as dimethylformamide, or cyclic ethers, such as tetrahydrofurane or dioxane. Instead of the free 16,17-diol it is also possible to use a corresponding 16-ester with a lower aliphatic monocarboxylic acid, for example formic acid, propionic acid, butyric acid, isobutyric acid, valeric acid, isovaleric acid or caproic acid, and especially acetic acid; the liberation of the diol is then carried out under the reaction conditions of the ketalisation or acetalisation. Equally, it is possible to employ, instead of the free carbonyl compound, a reactive derivative thereof, for example an acetal or ketal derived from a lower alkanol, especially methanol or ethanol, or an enol acylate, for example an enol acetate, or to employ a mixture of the free ketone and its derivative. In the case of aldehydes it is also possible to use their oligomers, for example trimers, such as para-acetaldehyde.

Those of the new compounds in which X represents fluorine or chlorine can also be prepared, for example, by treating an oxide of the formula

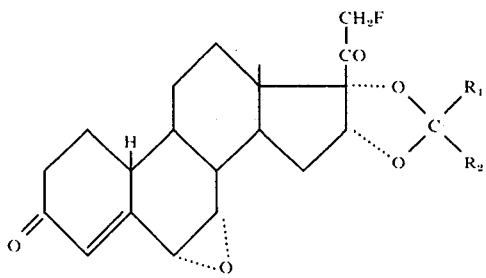

(VIII)

wherein $R_1$ and $R_2$ have the abovementioned meanings, with hydrogen chloride or hydrogen fluoride or a donor thereof and, if necessary, dehydrating a 6β-halogeno-7β-hydroxy compound obtained as an intermediate.

If it is desired that the process should lead in one step to the end product, it is advantageous to use concentrated hydrofluoric acid or hydrochloric acid in a suitable solvent, for example a chlorinated hydrocarbon, such as chloroform or methylene chloride, in a ketone, such as acetone, or especially in a lower aliphatic monocarboxylic acid, such as propionic acid or butyric acid and above all in acetic acid. If it is desired to isolate the 6β-halogeno-7α-hydroxy compound which arises as an intermediate product, it is advantageous to use a donor of the particular hydrogen halide, for example a pyridinium salt or oxonium salt of the particular hydrogen halide acid, such as pyridinium hydrochloride or a complex of hydrogen fluoride with tetrahydrofurane or dioxane or, for example, a complex of hydrogen fluoride with urea or dimethylformamide. The subsequent dehydration can be effected by treatment with concentrated hydrogen halide acid, preferably hydrochloric acid, in a lower aliphatic monocarboxylic acid, for example one of those mentioned above.

Depending on the choice of the procedure and of the starting substances, the new compounds according to the invention can be in the form of isomer mixtures. This occurs in the case of compounds in which the substituents $R_1$ and $R_2$ defined above are not identical or the carbonyl component contains asymmetrical carbon atoms. Such epimer mixtures which may be obtained can be separated into their epimeric compounds in a known manner on the basis of the physico-chemical differences of the components, for example by chromatography and/or fractional crystallisation.

The invention also relates to those embodiments of the above processes in which a compound obtainable as an intermediate product at any stage is used as the starting material and the missing steps are carried out or in which a starting material is formed under the reaction conditions.

The starting materials for the processes of the present invention are known or can be manufactured in a manner which is in itself known. Thus, for example, most of the starting materials of the 19-norpregnane series can be obtained from their 10-methyl analogues (that is to say the corresponding compounds of the pregnane series) by the multi-stage degradation of the angular 10-methyl group, which as a method is in itself known. This degradation consists in principle of the following stages: a) a transannular oxidation of the angular methyl group, preferably by treatment of a suitable 6β-hydroxy compound with lead tetraacetate in a manner which is in itself known, to form a 6β,19-oxido bridge, b) splitting of this 6β,19-oxido bridge, if appropriate under oxidative or reductive conditions, with the simultaneous production of a group containing oxygen, such as a carbinol, formyl or carboxyl group, in the 19-position, and of a double bond in the 4,5- or 5,6-position and optionally additionally in the 6,7-position; c) splitting off the group in the 19-position, with the formation of the 19-nor derivative. If, in this process, simpler or unsubstituted base materials are used, it is possible to interpolate, at a suitable stage of the above degradation process, desired transformations, for example the introduction of the 6-halogen, the epoxidation of the 6,7-double bond, the 16,17-ketalisation, the introduction of the fluorine in the 21-position or the formation of the 16α,17α-diol grouping, again proceeding in a manner which is in itself known, for example as described above for the individual processes.

The present invention also relates to the manufacture of pharmaceutical preparations for use in human or veterinary medicine and of contraceptives for humans and mammals, which contain the new pharmacologically active materials of the present invention, described above, as active substances, together with a pharmaceutical excipient. The excipients used are organic or inorganic materials which are suitable for enteral, for example oral, parenteral or topical administration. Suitable materials for forming these are materials which do not react with the new compounds, such as, for example, water, gelatine, lactose, starch, magnesium stearate, talc, vegetable oils, benzyl alcohols, gum, polyalkylene glycols, white petroleum jelly, cholesterol and other known medicinal excipients. The pharmaceutical preparations can be in a solid form, for example as tablets, dragees or capsules, or in a liquid or semi-liquid form, as solutions, suspensions, emulsions, ointments or creams. These pharmaceutical preparations are optionally sterilised and/or contain auxiliaries, such as preservatives, stabilisers, wetting agents or emulsifiers, salts for regulating the osmotic pressure or buffers. They can also contain yet other therapeutically valuable or pharmacologically active materials.

The compounds of the present application can also be used as feeding-stuff additives.

The invention is described in more detail in the examples which follow, without thereby limiting its scope.

EXAMPLE 1

Crude 21-fluoro-16α,17α-isopropylidenedioxy-3,20-dioxo-4,6-pregnadienoic-19-acid is dissolved in 50 ml of glacial acetic acid, after which the mixture is allowed to boil for 15 minutes under reflux in a stream of nitrogen. It is then evaporated in vacuo, the residue is dissolved in toluene and the solution is again evaporated in vacuo. The residue thus obtained is dissolved in toluene and the solution is filtered through 5.3 g of aluminum oxide (activity II), which is rinsed with 500 ml of a toluene:ethyl acetate (4:1) mixture. Crystallisation, from methylene chloride/ether, of the residue from evaporating the filtrate in vacuo, gives 21-fluoro-16α,17α-isopropylidenedioxy-19-nor-4,6-pregnadiene-3,20-dione of melting point 257°–263° C.

21-Fluoro-16α,17α-isopropylidenedioxy-3,20-dioxo-4,6-pregnadienoic-19-acid, used as the starting material, is manufactured, for example, as follows:

16α,17α-Epoxy-21-fluoro-3β-hydroxy-5-pregnen-20-one, on acetylation and treatment with hydrogen bromide, renewed acetylation of the resulting 3β- acetoxy-16β-bromo-21-fluoro-17α-hydroxy-5-pregnen-20-one to give 3β,17α-diacetoxy-16β-bromo-21-fluoro-5-pregnen-20-one, reaction thereof with sodium acetate in glacial acetic acid to give 3β,16α-diacetoxy-21-fluoro-17α-hydroxy-5-pregnan-20-one and successive treatment of the latter with acetone, methanol, hydrochloric acid and pyridine-acetic anhydride gives, in a manner which is in itself known, 3β-acetoxy-21-fluoro-16α,17α-isopropylidenedioxy-5-pregnen-20-one.

4.55 ml of water are added to a mixture of 9.19 g of 3β-acetoxy-21-fluoro-16α,17α-isopropylidenedioxy-5-pregnen-20-one, 91.ml of dioxane and 6.64 ml of 13.5 percent strength perchloric acid, and thereafter 4.55 g of N-bromoacetamide are added over the course of 15 minutes whilst stirring and cooling with ice. After stirring for 30 minutes at room temperature, the mixture is cooled and 54.6 ml of 1 percent strength sodium thiosulphate solution are added. This mixture is extracted twice with ether and after washing with water and drying with sodium sulphate the extract is evaporated in vacuo. Crystallisation from a methylene chloride/ether mixture gives 3β-acetoxy-5α-bromo-21-fluoro-6β-hydroxy-16α,17α-isopropylidenedioxy-5α-pregnan-20-one of melting point 157°–163° C (decomposition).

34 g of lead tetraacetate, containing approx. 10 to 15% of acetic acid, 15.5 g of calcium carbonate and 800 ml of cyclohexane are initially introduced into a sulphonation flask. After boiling for 10 minutes whilst stirring, 6.72 g of 3β-acetoxy-5α-bromo-21-fluoro-6β-hydroxy-16α,17α-isopropylidenedioxy-5α-pregnan-20-one and 7.34 g of iodine are added to the hot solution. The mixture is then allowed to continue to boil for 40 minutes whilst being exposed to a 500 Watt lamp and is thereafter cooled and filtered through Celite, which is rinsed with methylene chloride. The filtrate is stirred for 30 minutes with 3 l of 10 percent strength sodium thiosulphate solution. The aqueous phase is re-extracted with methylene chloride and the organic phases are washed with water, dried and evaporated in vacuo. Crystallisation from a methylene chloride/ether mixture gives 3β-acetoxy-5α-bromo-6β,19-epoxy-21-fluoro-16α,17α-isopropylidenedioxy-5α-pregnan-20-one which after further recrystallisation from the same solvent mixture melts at 254.5°–256° C.

A solution of 3.7 g of potassium carbonate in 37 ml of water, followed by 3.72 g of 3β-acetoxy-5α-bromo-6β,19-epoxy-21-fluoro-16α,17α-isopropylidenedioxy-5α-pregnan-20-one, are added to 370 ml of methanol in a stream of nitrogen. After boiling for one hour under reflux, the mixture is concentrated in vacuo, diluted with water and extracted with methylene chloride. The organic phases are washed with water, dried and evaporated in vacuo. Recrystallisation of the residue from methylene chloride/ether gives 3β-hydroxy-5α-bromo-6β,19-epoxy-21-fluoro-16α,17α-isopropylidenedioxy-5α-pregnan-20-one of melting point 238°–239° C. Further recrystallisation raises the melting point to 240°–241° C.

5 ml of 8 N chromic acid (Kiliany solution) are added over the course of 2 minutes to a solution of 3.16 g of 3β-hydroxy-5α-bromo-6β,19-epoxy-21-fluoro-16α,17α-isopropylidenedioxy-5α-pregnan-20-one in 150 ml of acetone at an internal temperature of 0° C, whilst stirring and cooling with an ice/methanol mixture. 15 minutes later, a solution of 20 g of sodium acetate in 100 ml of water is added. The mixture is then extracted with toluene and the organic extracts are washed with water. After evaporation in vacuo, the residue is taken up in pyridine in order to complete the elimination of hydrogen bromide. The mixture is then diluted with methylene chloride, washed with sodium bicarbonate solution and water, dried and evaporated in vacuo. Crystallisation from methylene chloride/ether gives 6β,19-epoxy-21-fluoro-16α,17α-isopropylidenedioxy-4-pregnene-3,20-dione of melting point 276°–279° C.

15.69 g of 6β,19-epoxy-21-fluoro-16α,17α-isopropylidenedioxy-4-pregnene-3,20-dione are added to a solution of 2.64 g of p-toluenesulphonic acid in 21.2 ml of glacial acetic acid and 14.4 ml of acetic anhydride, under a stream of nitrogen, the material being rinsed down with 1 ml of glacial acetic acid. After stirring for one hour in a stream of nitrogen at a bath temperature of 106° C, 5.52 g of sodium acetate are added and the mixture is cooled and poured into 800 ml of water. This mixture is then repeatedly extracted with methylene chloride, and the extracts are washed with sodium bicarbonate solution and water, dried and evaporated in vacuo. The residue from two such batches is chromatographed on 1.5 kg of silica gel. The fractions eluted with a toluene/ethyl acetate (19:1) mixture give a little 3-acetoxy-21-fluoro-16α,17α-isopropylidenedioxy-19-nor-1,3,5(10)-pregnatrien-20-one. 19-Acetoxy-21-fluoro-16α,17α-isopropylidenedioxy-4,6-pregnadiene-3,20-dione is eluted with a toluene/ethyl acetate (9:1) mixture. After recrystallisation from methylene chloride/ether mixture, crystals which on further recrystallisation melt at 161°–163° C, are obtained.

A solution of 24.5 g of sodium bicarbonate in 300 ml of water is added to a boiling solution of 17.5 g of 19-acetoxy-21-fluoro-16α,17α-isopropylidenedioxy-4,6-pregnadiene-3,20-dione in 770 ml of methanol under a stream of nitrogen. After boiling for 2 hours under reflux, the mixture is cooled and poured out into water, and this mixture is repeatedly extracted with methylene chloride. The organic phases are washed with water, dried and evapoated in vacuo, and crystallisation of the residue from methylene chloride/ether mixture gives 21-fluoro-19-hydroxy-16α,17α-isopropylidenedioxy-4,6-pregnadiene-3,20-dione of melting point 240°–243° C.

1.68 ml of 8 N chromic acid (Kiliany solution) are added to a solution of 537.5 mg of 21-fluoro-19-hydroxy-16α,17α-isopropylidenedioxy-4,6-pregnadiene-3,20-dione in 17 ml of acetone whilst stirring and cooling with ice/water. 25 minutes later, 1 ml of methanol is added and after a further 5 minutes the mixture is poured into water. After repeated extraction by shaking with methylene chloride, the extracts are washed with water, dried and evaporated in vacuo, giving the desired crude 21-fluoro-16α,17α-isopropylidenedioxy-3,20-dioxo-4,6-pregnadienoic-19-acid.

EXAMPLE 2

2.47 g of 6α,7α-epoxy-21-fluoro-16α,17α-isopropylidienedioxy-19-nor-4-pregnene-3,20-dione are dissolved in 340 ml of chloroform saturated with hydrochloric acid. 30 minutes later, the mixture is washed with saturated sodium bicarbonate solution and water. The aqueous solutions are re-extracted with methylene chloride, after which the organic phases are dried with sodium sulphate and evaporated in vacuo. The residue is dissolved in toluene and the solution is filtered through 20 g of silica gel, which is rinsed with 500 ml of a toluene-ethyl acetate (9:1) mixture. After evaporating the filtrate in vacuo, the residue is recrystallised from methylene chloride/ether. Pure 6-chloro-21-fluoro-16α,17α-isopropylidenedioxy-19-nor-4,6-pregnadiene-3,20-dione of melting point 235° – 236.5° C is obtained.

The 6,7-oxido compound used as the starting material can be prepared as follows:

A solution of 2 g of 21-fluoro-16α,17α-isopropylidenedioxy-19-nor-4,6-pregnadiene-3,20-dione and 2 g of m-chloroperbenzoic acid in 125 ml of methylene chloride is left to stand for 22 hours at room temperature. It is then poured into 2 N sodium hydroxide solution and the mixture is extracted three times with toluene. The organic solutions are washed three times with 2 N sodium hydroxide solution and three times with water, dried and evapoated in vacuo. Crystallisation of the residue from methylene chloride/ether gives 6α,7α-epoxy-21-fluoro-16α,17α-isopropylidenedioxy-19-nor-4-pregnene-3,20-dione of melting point 248°–253° C.

EXAMPLE 3

9.75 ml of a 5 percent strength solution of benzyl alcohol in ethanol are added to a boiling mixture of 1.3 g of 21-fluoro-16α,17α-isopropylidenedioxy-6-methylene-19-norpregn-4-ene-3,20-dione, 455 mg of 5 percent strength palladium on charcoal and 65 ml of ethanol. 3¾ hours later, a suspension of 455 mg of 5 percent strength palladium on charcoal in 65 ml of ethanol is added, followed by a further 9.75 ml of a 5 percent strength solution of benzyl alcohol in ethanol. After boiling for a total period of 5 hours, the mixture is filtered through Celite, the latter being rinsed with methylene chloride, and the filtrate is washed with saturated sodium chloride solution, dried and evaporated in vacuo. The residue is then dissolved in methylene chloride and the solution is filtered through 84.5 g of silica gel which is rinsed with 6.4 l of methylene chloride. The residue from the first 1.6 l is discarded. After evaporating the next 4.8 l in vacuo, 1.08 g of a crystalline residue remain. This is added to 108 ml of a 2 N solution of hydrochloric acid in dioxane and 540 mg of 2,3-dichloro-5,6-dicyano-benzoquinone are then added whilst stirring. After 1½ hours, the product is filtered off and rinsed with toluene. The filtrate is washed with water, 1 percent strength sodium hydroxide solution and water, dried and evaporated in vacuo. The residue is then chromatographed on 30 g of silica gel, using fractions each of 500 ml of methylene chloride. The residue from fractions 2-4 is separated on 6 plates of silica gel, each of 1 m, using a toluene/acetone (19:1) mixture as the migrating agent. Pure 21-fluoro-16α,17α-isopropylidenedioxy-6-methyl-19-norpregna-4,6-diene-3,20-dione of melting point 226°–228° C is thus obtained.

The 21-fluoro-16α,17α-isopropylidenedioxy-6-methylene-19-norpregn-4-ene-3,20-dione used as the starting material is prepared as follows.

6.56 g of 21-fluoro-16α,17α-isopropylidenedioxy-19-norpregna-4,6-diene-3,20-dione described in Example 1, 545 mg of 10 percent strength palladium on calcium carbonate and 327 ml of dimethylformamide are shaken in a hydrogen atmosphere until 1 mol equivalent of hydrogen has been taken up. After filtering off the catalyst, the filtrate is diluted with water and the mixture is again filtered. 21-fluoro-16α,17-isopropylidenedioxy-19-norpregn-4-ene-3,20-dione thus obtained melts at 258°–261° C after recrystallisation from methylene chloride/ether. 400 mg of this compound, 40 mg of p-toluenesulphonic acid, 10 ml of dioxane and 0.68 ml of orthoformic acid methyl ester are stirred for 16 hours at room temperature in a nitrogen atmosphere. 0.32 ml of pyridine is then added and the mixture is poured into 40 ml of water and 4.8 ml of saturated sodium bicarbonate solution. After stirring for three hours, the product is filtered off, washed with water and dried in vacuo over phosphorus pentoxide. 422 mg of crude 21-fluoro-16α,17-isopropylidenedioxy-3-methoxy-19-norpregna-3,5-dien-20-one are obtained. This can be purified 180° C. 2.2 ml of phosphorus oxychloride are added to a mixture of 20 ml of methylene chloride and 2.6 ml of dimethylformamide whilst stirring and cooling with an ice/methanol mixture. 15 minutes later 3.91 g of the methoxydiene obtained above are added and rinsed down with 5 ml of methylene chloride. After stirring for two hours whilst cooling with ice/water, the cooling bath is removed and the mixture is stirred for a further hour. A mixture of 8.8 g of sodium acetate and 28 ml of 90 percent strength methanol is then again added whilst cooling with ice/water and 30 minutes later the mixture is diluted with methylene chloride and washed with 2 N sodium carbonate solution and water. The residue obtained after drying and evaporation in vacuo is dissolved in toluene and the solution is filtered through 40 g of silica gel, which is rinsed with 3 l of toluene. Crystallisation of the residue from this filtrate, from methylene chloride/ether, gives 3.5 g of 21-fluoro-6-formyl-16α,17-isopropylidenedioxy-3-methoxy-19-norpregna-3,5-dien-20-one. $\epsilon_{220} = 7,800$; $\epsilon_{323} = 11,700$ (fine spirit). A solution of 460 mg of sodium borohydride in 4.6 ml of 1 N sodium hydroxide solution is added to a mixture of 3.66 g of this compound and 37 ml of methanol, whilst stirring, and 1κ hours later a mixture of 3 ml of concentrated hydrochloric acid and 1.5 ml of water is allowed to run in slowly whilst cooling with ice/water. After half an hour, 4.6 g of sodium acetate and water are added, and the product is then filtered off, washed with water and dried in vacuo over phosphorus pentoxide. The residue thus obtained is mixed with 82.5 ml of acetone and 20.5 ml of methylene chloride and 3.25 ml of Kiliany solution are then slowly added dropwise whilst cooling with ice. After stirring for 1¾ hours at 0° C, a further 0.8 ml of Kiliany solution is added. 15 minutes later, 825 ml of a 10 percent strength sodium acetate solution are added and the mixture is extracted with methylene chloride. The extract is washed with sodium bicarbonate solution and water, dried and evaporated in vacuo. The residue is chromatographed on 90 g of silica gel. 21-Fluoro-16α,17-isopropylidenedioxy-6-methylene-19-norpregn-4-ene-3,20-dione is eluted with a toluene/ethyl acetate (19:1) mixture. After recrystallisation from methylene chloride/ether, 1.6 g are obtained; $\epsilon_{267} = 11,100$ (fine spirit).

Example 4:

| Composition per tablet: | |
|---|---|
| 21-Fluoro-16α,17α-dihydroxy-19-nor-4,6-pregnadiene-3,20-dione-16,17-acetonide | 2.0 mg |
| Lactose | 139.0 mg |
| Colloidal silica (Aerosil) | 10.0 mg |
| Wheat starch | 42.0 mg |
| Talc | 6.0 mg |
| Magnesium stearate | 1.0 mg |
| | 200.0 mg |

The active substances are mixed homogeneously with a part of the lactose. This premix is mixed with the remaining lactose, the colloidal silica and a part of the starch, moistened with water and granulated, and dried, in the usual manner. The remaining starch, talc and magnesium stearate are mixed with the dry granules and the homogeneous mixture is pressed to form tablets weighing 200.0 mg.

Tablets containing 1.0 mg of 21-fluoro-16α,17α-dihydroxy-6-methyl-19-nor-4,6-pregnadiene-3,20-dione-16,17-acetonide or 6-chloro-21-fluoro-16α,17α-dihydroxy-19-nor-4,6-pregnadiene-3,20-dione-16,17-acetonide are manufactured analogously.

We claim:

1. A 21-fluoro-19-norpregnadiene compound of the general formula

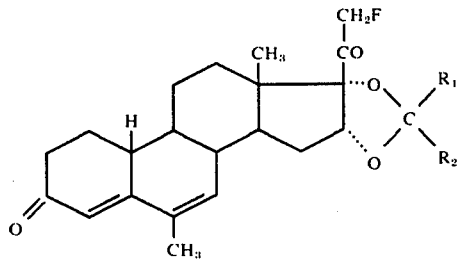

wherein $R_1$ and $R_2$ each individually denote a lower alkyl, lower cycloalkyl, phenyl or benzyl radical or together with the adjacent carbon atom form the cyclopentane or the cyclohexane ring.

2. A 21-fluoro-19-nor-4,6-pregnadiene compound of claim 1 characterized by the formula I, wherein X represents methyl and $R_1$ and $R_2$ have the meanings indicated in claim 1.

3. A compound of claim 1, which compound is 21-fluoro-16α,17α-dihydroxy-6-methyl-19-nor-4,6-pregnadiene-3,20-dione-16,17-acetonide.

4. A compound of claim 1, which compound is 21-fluoro-16α,17α-dihydroxy-6-methyl-19-nor-4,6-pregnadiene-3,20-dione-16,17-cyclopentanonide.

* * * * *